United States Patent
Turumaki et al.

(10) Patent No.: US 9,283,384 B2
(45) Date of Patent: Mar. 15, 2016

(54) ELECTRICAL LIVING BODY STIMULATION SIGNAL WAVEFORM GENERATION DEVICE AND ELECTRICAL LIVING BODY STIMULATION DEVICE

(71) Applicants: EXCARE JAPAN CO., LTD., Chiyoda-ku, Tokyo (JP); TECHNO KABUSHIKI KAISHA, Sagara-gun, Kyoto (JP)

(72) Inventors: Masaei Turumaki, Nara (JP); Ryoji Kawahata, Yamato (JP)

(73) Assignee: EXCARE JAPAN CO., LTD., Tokyo (JP)

( * ) Notice: Subject to any disclaimer, the term of this patent is extended or adjusted under 35 U.S.C. 154(b) by 7 days.

(21) Appl. No.: 14/075,059

(22) Filed: Nov. 8, 2013

(65) Prior Publication Data
US 2014/0067009 A1    Mar. 6, 2014

Related U.S. Application Data

(63) Continuation of application No. PCT/JP2012/063579, filed on May 22, 2012.

(30) Foreign Application Priority Data

Jul. 12, 2011 (JP) .................................. 2011-165998

(51) Int. Cl.
*A61N 1/36* (2006.01)

(52) U.S. Cl.
CPC ........ *A61N 1/36003* (2013.01); *A61N 1/36071* (2013.01); *A61N 1/36078* (2013.01)

(58) Field of Classification Search
CPC ........... A61N 1/36003; A61N 1/36071; A61N 1/36078
USPC ................................................ 607/2, 48, 115
See application file for complete search history.

(56) References Cited

U.S. PATENT DOCUMENTS

| | | | | |
|---|---|---|---|---|
| 5,507,781 | A * | 4/1996 | Kroll et al. .................. | 607/7 |
| 7,423,401 | B2 * | 9/2008 | Kinpara et al. ............... | 318/490 |
| 2002/0072770 | A1 * | 6/2002 | Pless ........................ | 607/2 |
| 2002/0077670 | A1 * | 6/2002 | Archer et al. ................. | 607/45 |
| 2004/0073273 | A1 * | 4/2004 | Gluckman et al. ............. | 607/48 |
| 2004/0236391 | A1 * | 11/2004 | Kobayashi et al. ............. | 607/72 |
| 2006/0155341 | A1 * | 7/2006 | Tehrani et al. ................. | 607/42 |
| 2008/0275343 | A1 * | 11/2008 | Hoffmann .................... | 600/439 |

(Continued)

FOREIGN PATENT DOCUMENTS

| | | |
|---|---|---|
| JP | H03-070155 U | 7/1991 |
| JP | H11-197255 A | 7/1999 |
| JP | 2001-259048 A | 9/2001 |
| JP | 2002-153565 A | 5/2002 |

(Continued)

*Primary Examiner* — Christopher A Flory
(74) *Attorney, Agent, or Firm* — Mots Law, PLLC

(57) ABSTRACT

An electrical living body stimulation signal waveform generation device includes a waveform generation unit that generates a low-frequency pulse signal wave and a high-frequency signal wave individually, and a waveform synthesis circuit that superimposes the high-frequency signal wave on the low-frequency pulse signal wave during an ON period of the low-frequency pulse signal wave to form a synthesized wave having a waveform in which a level gradually rises from a point of time when the superimposition is started and the ON period and an OFF period are continuously repeated, wherein the synthesized wave is given as an electrical stimulus to a living body.

9 Claims, 5 Drawing Sheets

(56) References Cited

U.S. PATENT DOCUMENTS

| | | | |
|---|---|---|---|
| 2008/0319509 A1* | 12/2008 | Laback et al. | 607/57 |
| 2012/0184801 A1* | 7/2012 | Simon et al. | 600/14 |
| 2012/0316624 A1* | 12/2012 | Smith et al. | 607/99 |
| 2014/0243941 A1* | 8/2014 | Rogers et al. | 607/112 |

FOREIGN PATENT DOCUMENTS

| | | |
|---|---|---|
| JP | 2004-216031 A | 8/2004 |
| JP | 2008-100086 A | 5/2008 |
| JP | 2010-057805 A | 3/2010 |
| JP | 2010-184113 A | 8/2010 |

* cited by examiner

ELECTRICAL LIVING BODY STIMULATION SIGNAL WAVEFORM GENERATION DEVICE AND ELECTRICAL LIVING BODY STIMULATION DEVICE

CROSS REFERENCE TO RELATED APPLICATIONS AND INCORPORATION BY REFERENCE

This application is a Continuation of PCT Application No. PCT/JP2012/063579, filed on May 22, 2012, and claims the priority of Japanese Patent Application No. 2011-165998, filed on Jul. 12, 2011; the entire contents of which are incorporated by reference herein.

BACKGROUND OF THE INVENTION

1. Field of the Invention

The present invention relates to an electrical living body stimulation signal waveform generation device and an electrical living body stimulation device, which give an electrical stimulus to a living body and thereby effectively offer muscle training, relaxation, figure improvement, muscle pain healing, fatigue recovery treatment, and the like.

2. Description of the Related Art

It is a widely known practice that electrodes (pads) are brought into contact with the surface of a living body and electrical pulse waves and electrical sine waves are given thereto, whereby an electrical stimulus is given to a muscle causing the muscle to be activated and relaxed. Electrotherapy devices and electrical health equipment, each of which uses such effects of the electrical stimulus, are put into practical use. Depending on the purpose, such devices and equipment are used in various ways such as for muscle stimulation, muscle rehabilitation, muscle training, figure improvement, relaxation, and further, treatments for muscle pain, stiffness, numbness, lumbago and fatigue recovery.

A large number of living body stimulation devices, each of which is based on such an electrical stimulus as described above, use low-frequency pulses. A low-frequency pulse current is allowed to flow between electrodes arranged on two or more spots on the living body, the stimulus is given to the muscle between the electrodes, and the muscle is repeatedly contracted and relaxed. In such a way, the bloodstream of the muscle is accelerated and physical effects such as shoulder tapping, massage therapy, and muscle training can be obtained.

As the low-frequency pulses of the electrotherapy device or the like, pulse waves of several hertz to several ten hertz are used. The voltage intensity of the pulses, the width of the pulses, the ON/OFF interval of the pulses thus generated, and the like are changed and are combined with one another, whereby a pulse waveform, which corresponds to a particular purpose such as shoulder tapping, muscle tone-up, and relaxation, is formed. For example, low-frequency therapy devices or the like which are commercially available at present, generate reference pulses with a pulse width from 0.2 milliseconds to several milliseconds at a pulse voltage from 10V to 20V. Then, in the shoulder tapping mode, the generation interval of the reference pulses is changed from several milliseconds to several seconds in response to preferences of a user, and a desired shoulder tapping effect is obtained. Moreover, in modes such as the massage effect and the relaxation effect, ten to several-ten groups of the above-described reference pulses are repeatedly turned on and off with cycles ranging from one to several seconds, whereby a manual massage effect is obtained.

Although definitions of a low frequency and a high frequency are not definite, low frequency generally stands for a frequency of less than 20 kHz in this industrial field (electrotherapy field), and high frequency stands for a frequency of 20 kHz or more. Moreover, in the case of including the concept of a medium frequency, a frequency of less than 1 kHz is defined as the low frequency, a frequency of 1 kHz to less than 10 kHz is defined as the medium frequency, and a frequency of 10 kHz or more is defined as the high frequency. When the low-frequency pulses are given to the muscle, the muscle is stimulated and contracted. However, when such pulse waves are thereafter paused, the muscle starts to relax. In the shoulder tapping mode or the like, low-frequency pulses of several hertz to several ten hertz are used, and every time each of the low-frequency pulses is given, the muscle is relaxed, and there is brought about a shoulder tapping effect with a feeling like "tap, tap . . . ." Moreover, when the frequency of the low-frequency pulses is increased, and where, before the muscle starts to be relaxed, the next pulse is continuously given without any interval, then the contracted state of the muscle is held. Thereafter, an interval state thereof where the pulses are paused is brought about, whereby the muscle turns to a relaxed state, and an effect that the muscle is massaged slowly is created.

In this type of low-frequency pulse therapy device, rectangular pulses are usually used. Therefore, owing to the pulse stimulus caused by a sudden voltage change, there occurs a stimulation feeling like prickling (or sticking, shaking). A variety of proposals have been made in order to solve such an uncomfortable feeling. For example, a method of absorbing the stimulation feeling, by alternately changing positive and negative polarities of the low-frequency rectangular pulses to be given, is put into practical use in many electrical stimulation therapy devices. Moreover, by using the fact that a stimulus given to a living body by sine waves is generally weaker in comparison with that given thereto by the rectangular pulse waves, sine wave components are mixed into the rectangular pulses. Methods devised in various ways, which include this mixing, have also been proposed.

For example, PWM (pulse width modulation) pulses are used as ON pulses, and components with a frequency higher than that of the low-frequency rectangular pulses are mixed therewith, and the pulse width is gradually widened from the rise of each pulse at the start of each ON pulse. Then, the pulse concerned is changed so that the pulse width thereof can be gradually made narrower as the pulse orbit thereof is passing through a half of the predetermined pulse width and approaching the drop portion. In such a way, a waveform approximate to sine waves is obtained, and a feeling of softness is obtained.

Moreover, as represented by the low-frequency therapy device, the electrical living body stimulation device is mainly used for stimulation of a surface muscle called an outer muscle. However, for stimulation of an inner muscle (deep muscle) present largely in a deep portion of the living body, no effective method has been proposed. If the interval between the electrodes is set as narrow as possible and the applied voltage is increased, then it is also possible to give a stimulus that reaches the inner muscle to a certain extent. However, there are limitations on the size of the applied voltage because the living body stimulation is intensified and because such a problem as skin burn also occurs. Therefore, using this method of increased voltage is not realistic. As a method for solving these problems, there is also proposed a method of giving the stimulus to the deep muscle using high-frequency pulses by superimposing the high-frequency pulses on the low-frequency pulses.

However, in this method, though such high-frequency components reach the deep muscle, a stimulation feeling occurs at the time of the rise of the low-frequency rectangular pulses since a waveform created by superimposition of the low-frequency rectangular pulses and the high-frequency pulses is used. That is to say, owing to the stimulation feeling like prickling (or sticking, shaking), long-time use and daily positive use of the device are hindered.

SUMMARY OF THE INVENTION

An aspect of the present invention is an electrical living body stimulation signal waveform generation device including: a waveform generation unit that generates a low-frequency pulse signal wave and a high-frequency signal wave individually; and a waveform synthesis circuit that superimposes the high-frequency signal wave on the low-frequency pulse signal wave during an ON period of the low-frequency pulse signal wave to form a synthesized wave having a waveform in which a level gradually rises from a point of time when the superimposition is started and the ON period and an OFF period of the low-frequency pulse signal wave are continuously repeated, wherein the synthesized wave is given as an electrical stimulus to a living body.

Another aspect of the present invention is an electrical living body stimulation device including: a waveform generation unit that generates a low-frequency pulse signal wave and a high-frequency signal wave individually; a waveform synthesis circuit that superimposes the high-frequency signal wave on the low-frequency pulse signal wave during an ON period of the low-frequency pulse signal wave to form a synthesized wave in which a level gradually rises from a point of time when the superimposition is started; an output control circuit that sets an output level of the synthesized wave; and a microcomputer that controls the waveform generation unit, the waveform synthesis circuit and the output control circuit so as to control at least any of a plurality of parameters including the output level of the synthesized wave, a rising rate of the output level, and a cycle and ON/OFF periods of the low-frequency pulse signal wave, wherein the synthesized wave is given as an electrical stimulus to a living body.

DETAILED DESCRIPTION OF THE INVENTION

First Embodiments

Figure 1A:
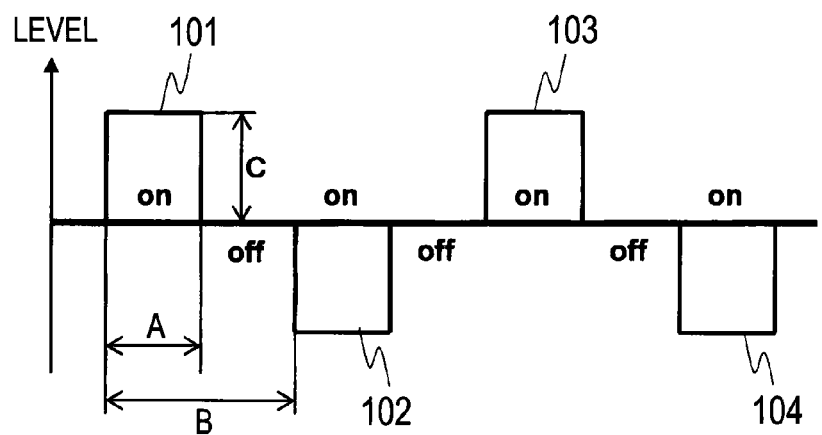
FIGS. 1A and 1B are explanatory charts of low-frequency waveforms according to a first embodiment of the present invention.

A description is made of the first embodiment of the present invention based on the drawings. The drawings are schematically illustrated for convenience of explanation. In FIG. 1A, rectangular wave pulses 101, 102, 103, 104 . . . repeat an ON period and an OFF period with a pulse width A over a cycle B at a level C. The pulse polarity in the ON state is periodically inverted, such that positive and negative are alternately repeated. Moreover, in FIG. 1B, saw tooth-like wave pulses 105, 106, 107, 108 . . . repeat the ON period and the OFF period with the pulse width A over the cycle B at the level C, the cycle B being the same as the cycle of the rectangular wave pulses. The pulse polarity in the ON state is periodically inverted, such that positive and negative are alternately repeated. Here, the ON period is a period while there occurs living body stimulation by low-frequency pulse signal waves, and the OFF period is a pause period of the living body stimulation. Note that, in FIG. 1A and FIG. 1B, with regard to the pulse polarity in the ON period, positive and negative are alternately repeated; however, the pulse signal waves are realizable even if the polarity thereof is fixed to either of positive and negative. Moreover, the saw tooth-like waves may be replaced by triangular waves.

Figure 1B:
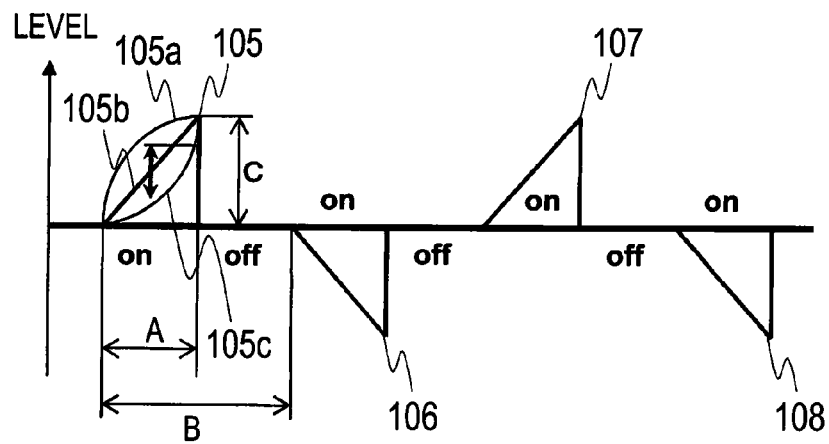

The level of each saw tooth-like wave (or the triangular wave) of FIG. 1B rises linearly (waveform 105b). However, a sine wave can be superimposed on this saw tooth-like wave by being added thereto or subtracted therefrom, whereby such a level can be prevented from rising linearly to create a non-linear waveform such as 105a or 105c. That is to say, the waveform can be changed by being raised to a large extent in the first half of the ON pulse state or being suddenly raised toward the second half of the ON pulse state.

Figure 2A:
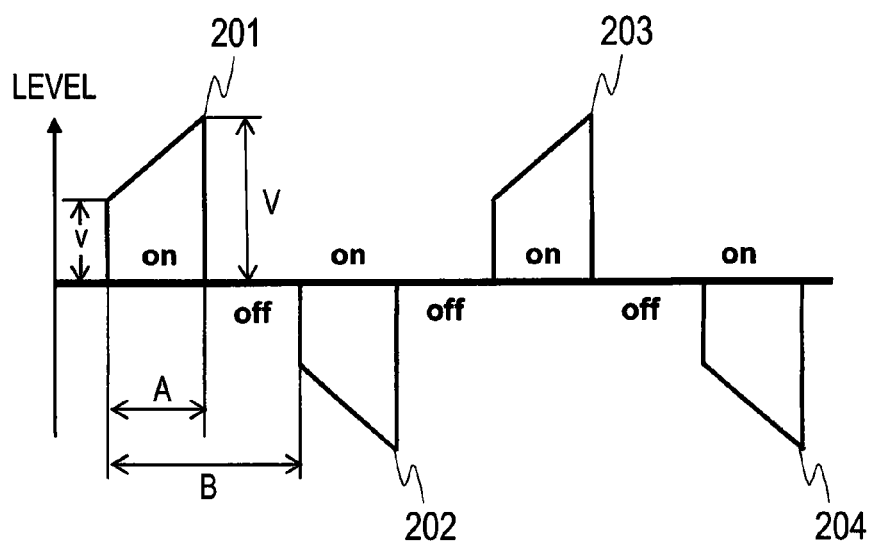
FIGS. 2A and 2B are explanatory charts of low-frequency synthesized waveforms according to the first embodiment of the present invention.
Figure 2B:
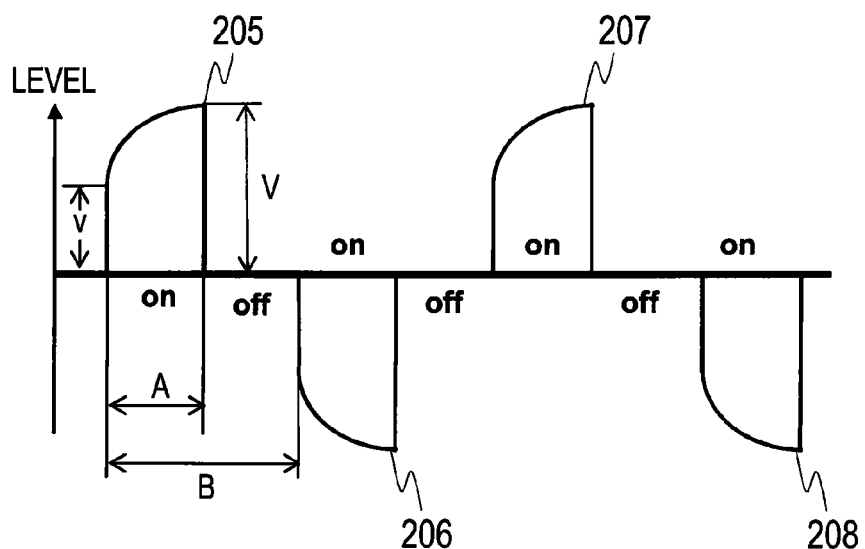

FIG. 2A shows a synthesized wave which is composed of a continuous wave of pulse waves 201, 202, 203, 204 . . . and is created by synthesizing the rectangular pulse waves shown in FIG. 1A and the saw tooth-like waves shown in FIG. 1B. FIG. 2B shows a synthesized wave which is composed of a continuous wave of low-frequency synthesized pulse waveforms 205, 206, 207, 208 . . . and is created by synthesizing the rectangular wave pulses of FIG. 1A not with the linearly increased waveform 105b of FIG. 1B but with the non-linearly increased waveform 105a thereof. Each of the pulse waves is shown with the pulse width A over the cycle B at a level V, and the frequency of the cycle B (second) is a low frequency from several hertz to several thousand hertz. The reason why the saw tooth-like waves and such pulse waves with the waveform 105a are superimposed on the rectangular wave pulses of FIG. 1A in the waveforms of FIG. 2A and FIG. 2B respectively, is that it is difficult to sense the stimulus to the living body if the stimulus concerned does not reach a certain level or more. The level of the low-frequency synthesized pulse waveform can be raised to a level v or more, and the level can be gradually changed from a point that exceeds the level v. This is because such a sense as described above is dependent on the body sensation of each individual and therefore varies among individuals. Accordingly, it is made possible to appropriately adjust the level v, and in addition, it is also made possible to variously change the shape of the rising curve (level raising method) as it rises.

In the case of giving the low-frequency synthesized pulse waves of FIG. 2A and FIG. 2B to the living body, a living body stimulation effect by the low-frequency pulses can be obtained. In this case, there is a stimulation effect substantially similar to that in the case of the rectangular wave pulses of FIG. 1A, and a contraction effect for the muscle is generated. However, since the level gradually rises, the prickling feeling at the time of the rise of each of the low-frequency synthesized pulse waves does not occur, and a relatively soft feeling is obtained. Moreover, at the time of the drop of each of the low-frequency synthesized pulse waves, though the stimulation feeling (prickling feeing) is absorbed to a certain extent, more than at the time of the rise thereof, a stimulation feeling due to a sudden drop and undershoot of each pulse concerned can be generated. However, if the drop of each of the low-frequency synthesized pulse waves is gradually attenuated and is formed into a shape approximate to a sine wave, then it is also possible to substantially prevent the stimulation feeling (prickling feeling) from being generated. The low-frequency synthesized pulse waves of FIG. 2A and FIG. 2B are set so as to absorb the stimulation feeling in the rising portions and to obtain some pulse simulation feeling in the dropping portions by using a steep drop.

Figure 3:
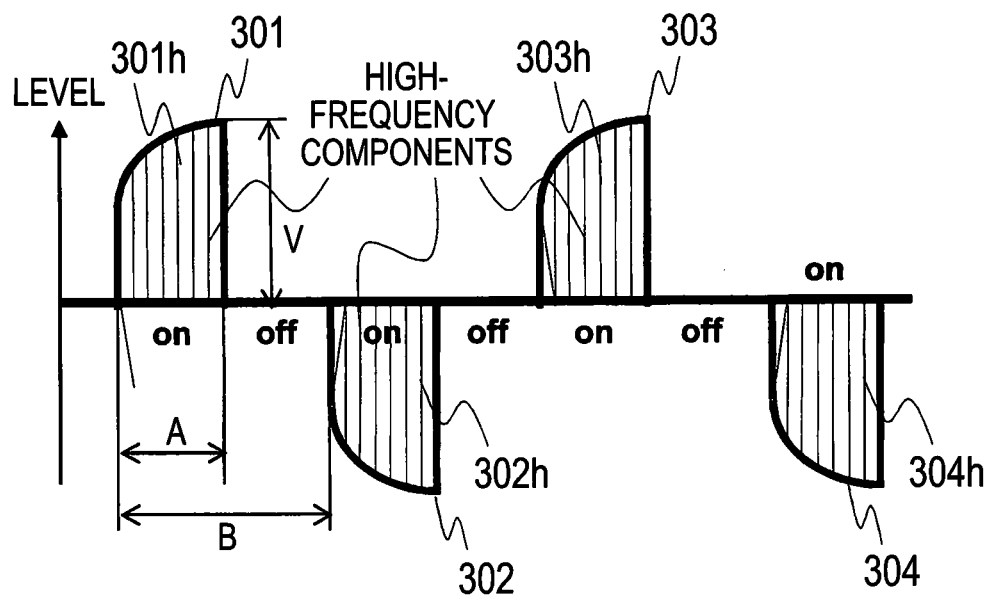
FIG. 3 is an explanatory chart of a synthesized waveform created by superimposing a high frequency on the low-frequency waveform according to the first embodiment of the present invention.

FIG. 3 shows a continuous pulse waveform composed of waveforms 301, 302, 303, 304 . . . created by superimposing high-frequency signals on ON portions of the low-frequency synthesized pulse waves (sword-like low-frequency synthesized waves) of FIG. 2B. If the frequency of the high-frequency signals is 10 kHz or more, then a stimulation effect for the deep muscle can be expected. In this embodiment, the stimulation effect for the deep muscle is obtained by using a frequency of approximately 500 kHz. High-frequency components 301h, 302h, 303h, and 304h are superimposed on the individual low-frequency synthesized pulse waves. The high-frequency components are used while appropriately changing the frequency thereof within a range from several kilohertz to several hundred kilohertz depending on the purpose. In general, as the frequency increases, a penetration effect of the stimulus for the deep muscle can be expected, and the stimulation feeling (prickling feeling) is sensed to be weak and fuzzy.

Figure 4:
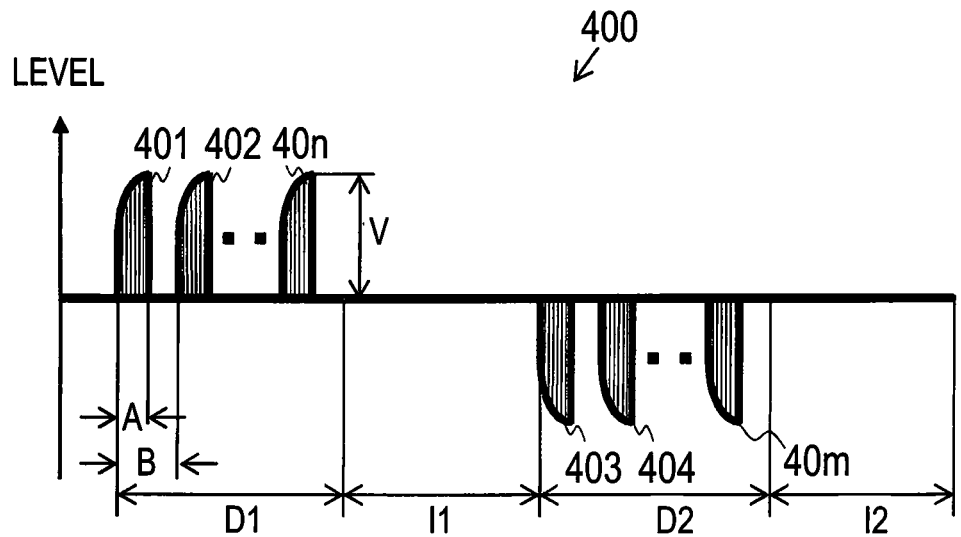
FIG. 4 is an explanatory chart of a waveform created by combining the synthesized waveforms according to the first embodiment of the present invention with one another.

FIG. 4 shows a continuous synthesized waveform 400 created by combining continuous generation periods of the synthesized wave pulses and interval/pause periods thereof based on the synthesized wave formed in FIG. 3. Hereinafter, this continuous synthesized waveform 400 is referred to as, "a continuous synthesized waveform of the sword-like synthesized waves" for convenience of explanation. In FIG. 4, during a first synthesized wave continuous generation period D1, n pieces of the sword-like synthesized pulse waves as shown in FIG. 3 are present and repeat ON and OFF. Hence, the ON period width of each pulse is represented as A, the cycle as a total sum of the ON period and an OFF period is represented as B, and the level of each pulse wave is represented as V. Such pulse waves here are created by combining n pieces of pulse waves 401, 402 . . . , all of which have the positive polarity; however, as shown in FIG. 3, the pulse wave may be a wave in which the polarity of pulse waves is alternately inverted.

After the synthesized wave continuous generation period D1, an interval/pause period I1 is provided. After the interval/pause period I1, during a synthesized wave continuous generation period D2, there is a continuous generation of synthesized pulses which are the inverse polarity of those during the synthesized wave continuous generation period D1. Setting is made so that m pieces of negative pulse waves 403, 404 . . . can be present and repeat ON and OFF. Moreover, after the synthesized wave continuous generation period D2, an interval/pause period I2 is set. A synthesized waveform created by continuously combining the synthesized wave continuous generation period D1 and the interval/pause period I1, and the synthesized wave continuous generation period D2 and the interval/pause period I2, is used for the living body stimulation. Here, depending on the purpose, the synthesized wave continuous generation periods D1 and D2 and the interval/pause periods I1 and I2 can be set to have the same period or can intentionally be set to be different from each other. That is to say, depending on the purpose, the number n of pulses and the number m of pulses present next thereto are set as the same number, or set to be different from each other, whereby it is also possible to impart rhythm changes or randomness to the stimulus for the living body.

In the case of giving the stimulus to the inner muscle (deep muscle) and the outer muscle (surface muscle) and attempting to obtain the effect of muscle training, figure improvement and the like, then, on the basis of the synthesized waveform as shown in FIG. 4, a variety of parameters such as the level and cycle length of each pulse, the number of pulses, and the interval/pause periods are controlled, whereby an appropriate stimulation waveform is generated and is given to the living body.

In general, the living body stimulation device or the pulse therapy device does not bring electrode terminals into direct contact with the skin of a human body or the like but gives the electrical stimulus to the living body through electrodes (pads). In the configuration of each of the electrodes, the electrode terminal of the stimulation device is covered with a material with high capacitive reactance such as rubber containing a conductive component such as carbon fiber, and is then brought into contact with the skin of the living body. In such a way, a direct current component with a high voltage is prevented from being directly given to the living body. Moreover, a living body such as a human body has capacitive reactance, and accordingly, by mixing the high-frequency component to the low-frequency pulses, it is made possible to give the living body stimulus to the deep muscle more deeply.

That is to say, an equivalent circuit in the case where the pulse waves are given as the living body stimulus is represented as one in which the pulse waves are given to a series circuit of a capacitor C and a resistor R. Therefore, it is conceived that, by mixing the high-frequency wave with the low-frequency pulses, current transmission is increased more, and the stimulation effect for the outer muscle (surface muscle) and the inner muscle (deep muscle) is obtained.

Figure 5:
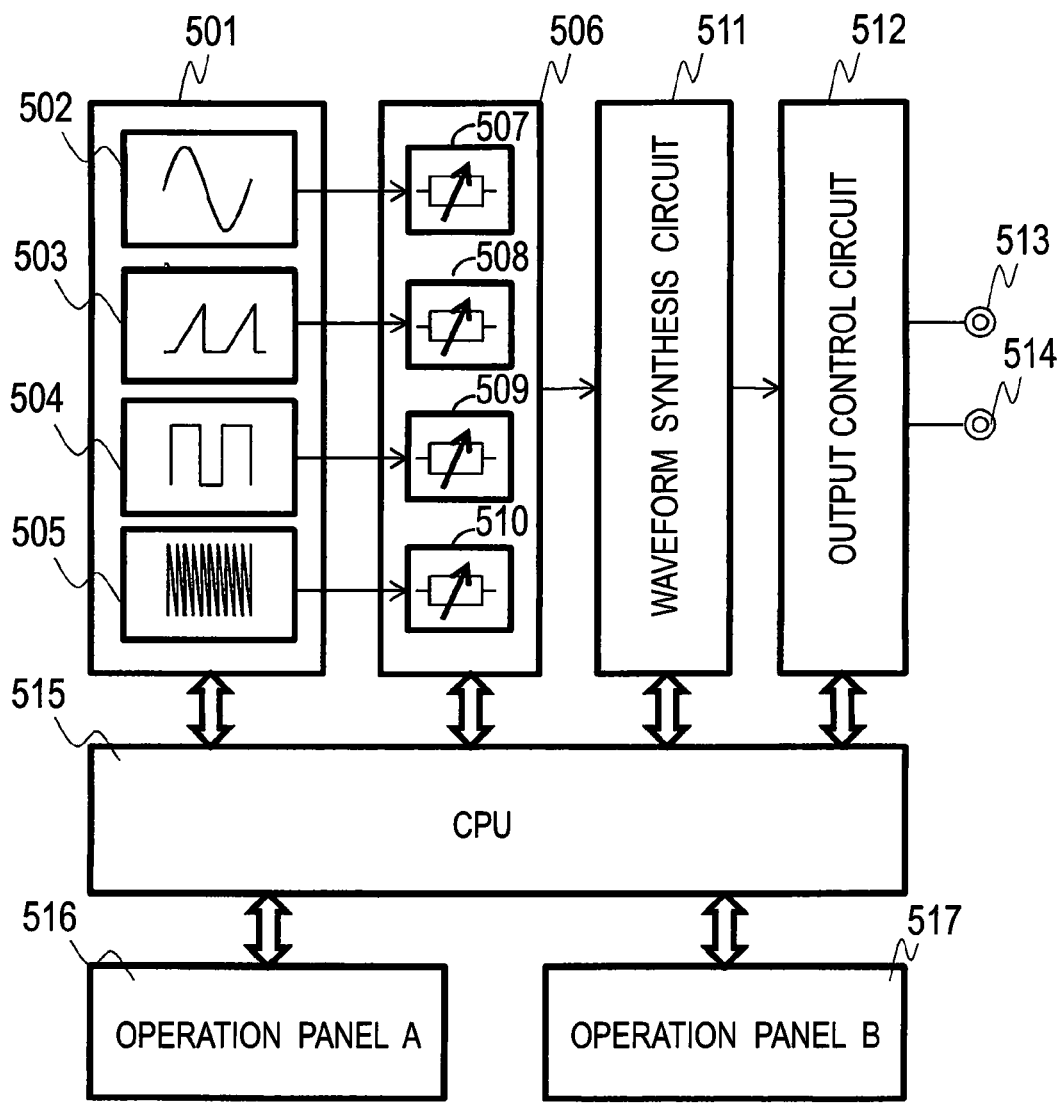
FIG. 5 is an explanatory block diagram of an electrical living body stimulation signal waveform generation device according to the first embodiment of the present invention.

FIG. 5 shows a circuit block diagram of the living body stimulation signal waveform generation device according to the first embodiment of the present invention. A waveform generation unit 501 includes a sine wave generator 502, a saw tooth-like wave generator 503, a rectangular wave generator 504, and a high-frequency signal generator 505, and with regard to individual outputs thereof, individual frequencies and levels of the outputs concerned are adjustable, and in addition, are made synchronizable with one another by the respective waveform adjusting circuits 507 to 510 of a waveform output control unit 506.

Outputs of the waveform output control unit 506 are individually sent to a waveform synthesis circuit 511. The waveform synthesis circuit 511 receives a control signal from a microcomputer (CPU) 515, and first, forms the low-frequency synthesized pulse waveform as shown in FIG. 2B. Then, the waveform synthesis circuit 511 superimposes the high-frequency components on the ON periods of the pulse waveform, forms the waveform as shown in FIG. 3, and outputs the formed waveform.

With regard to such an output signal formed in the waveform synthesis circuit 511, the output level V, the synthesized wave generation intervals D1 and D2, the interval/pause periods I1 and I2, and the like are adjusted in an output control circuit 512, and the synthesized waveform as shown in FIG. 4 is formed and outputted. Outputs of the output control circuit 512 are adapted to give the electrical stimulus to the living body through electrodes 513 and 514. In FIG. 5, only two electrodes 513 and 514 are illustrated; however, by providing three or four electrodes, the living body stimulation can also be given intensively to the muscle on a spot to be subjected to the treatment.

By an operation panel A 516, there is performed selection/input of a purpose mode such as muscle training, figure improvement, relaxation, and drainage (loosening up of muscle). By an operation panel B 517, an operation time (timer setting), intensity selection, and the like are inputted. Based on inputted instruction signals, the respective devices are controlled by the CPU 515 so as to form the living body stimulation waveforms suitable for the respective purposes. Parameters controlled by the CPU 515 are the ON period A, the cycle B as the total sum of the ON period A and the OFF period, and the level V of the synthesized waveform in the synthesized waveform 400 in FIG. 4, on which the high-frequency components are superimposed. In addition, the synthesized wave continuous generation periods D1 and D2 (number n or number m of the synthesized wave continuous generation pulses), the polarities of the pulses, the interval/pause periods I1 and I2, the number of repetitions thereof, and the like in FIG. 4 are also controllable parameters. The CPU 515 controls these parameters and generates the synthesized waveform pulses corresponding to the required purpose.

In this embodiment of the present invention, parameter settings for each mode is performed based on empirical data obtained from body sensations of many users. For example, in "muscle training mode", the output level V is raised and dropped several times in one second and is thereby set so as to obtain the feeling like "tap, tap . . . ." Moreover, in the case where the desired effect of this mode is to mainly stimulate the inner muscle, the cycle B is fixed and a frequency of approximately 2 kHz is given, whereby a body sensation is obtained in which the inner muscle is stimulated, and the muscle training of the deep inner muscles is obtained. "Figure improvement mode" is a mode for stimulating both of the inner muscle and the outer muscle, and the stimulus is prevented from being monotonous while shifting changes of the output width A and the cycle B. In "relaxation mode", the synthesized waveform of the low frequency and the high frequency is continuously outputted and only the cycle B is changed. Furthermore, in "drainage (loosening up of muscle) mode", the output level V is set at approximately 75% of the reference level such that the output is only weakly sensed. Moreover, for application to therapy, rehabilitation, or the like, the output level V can also be set so as to enable long-time use by using waveforms as shown in later-described FIG. 6A and FIG. 6B, in which no steep pulse change is generated. In particular, it is proven that, in a specific mode where the cycle B is changed always, periodically or randomly, a body sensation is obtained in which both of the inner muscle and the outer muscle are effectively stimulated. That is to say, it is conceived that the change of the cycle B largely affects the whole of the muscle stimulation function.

As a matter of course, it is also necessary to make it possible to use these parameters in an original setting (manual) mode by changing the these parameters in accordance with the preferences of the users and such senses thereof in the event of receiving the stimulus. Therefore, the waveform has been heretofore composed by including many waveform patterns using typical parameter settings corresponding to typical purposes. However, in the embodiment of the present invention, based on the reference pattern synthesized waveform configured in FIG. 4, the parameters of synthesized pulse groups are changed in a similar way and are combined with one another, whereby it is made possible to obtain a variety of the living body stimulation waveforms suitable for different user purposes. In this case, in the reference pattern synthesized waveform, groups of the parameters are: (1) a first group including a rising rate (waveform shape as shown in each of FIG. 4, FIG. 6A, and FIG. 6B) of the level of the synthesized waveform concerned, the pulse width A, the pulse cycle B, the pulse level V (reference level v), the synthesized wave continuous generation period D1 (number n of the synthesized pulses), and the interval/pause period I1: (2) a second group subsequent to the first group, which includes the polarities of the group of the synthesized pulses, the waveform shape thereof, the pulse width A, the pulse cycle B, the pulse level V (reference level v), the synthesized wave continuous generation period D2 (number m of the synthesized pulses), and the interval/pause period I2; and (3) a third group and after, which are subsequent to the second group.

As described above, in accordance with the living body stimulation signal waveform generation device according to the first embodiment of the present invention, by using the synthesized waves created by superimposing the high-frequency signal waves on the low-frequency pulse signal waves, it is possible to obtain the stimulation effect for the outer muscle (surface muscle) mainly by the function of the low-frequency components and the stimulation effect for the inner muscle (deep muscle) mainly by the function of the high-frequency signal waves. Then, the living body stimulation signal waveform generation device is configured so as to gradually raise the level of each synthesized wave from the point of time when the superimposition is started, whereby the prickling (shaking) feeling felt when receiving the pulse waves is reduced, and it is made possible to perform the living body stimulation, which ranges from the surface muscle to the depth muscle, by the soft stimulus.

Moreover, the high-frequency signal waves are superimposed on the low-frequency pulses formed by using the rectangular waves or the triangular waves. With regard to the level of the synthesized wave, the synthesized wave is formed into a waveform which gradually rises from the starting time of the superimposition, reaches the maximum at the ending time of the superimposition, and thereafter, is suddenly attenuated and turns to the OFF state. In such a way, the feeling is obtained in which the stimulus is gradually raised and is then released at the maximum point thereof.

Moreover, an electrical living body stimulation device can be configured which gives the electrical stimulus to the living body by using, as a basic waveform, the synthesized wave created by superimposing the high-frequency signal waves on the low-frequency pulse signal waves; the synthesization being performed by the above-described living body stimulation signal waveform generation device. That is to say, the electrical stimulus is given to the living body by using the waveform obtained by changing and combining multiple aspects of the synthesized wave; including, the level of the whole of the synthesized wave, the rising rate of the level, the cycle length, and the length of the ON/OFF periods. The basic waveform of the synthesized wave is changed variously, and the changed basic waves are combined variously with one another, whereby it is possible to effectively form signal waveforms corresponding to a variety of the living body stimulation purposes such as muscle training, relaxation, figure improvement, treatment for lumbago, and therapy for fatigue recovery. Furthermore, the variety of waveforms corresponding to a wide range of purposes can be composed by a simple circuit configuration, and it is therefore possible to provide an electrical living body stimulation device at low cost.

Second Embodiment

Figure 6A:
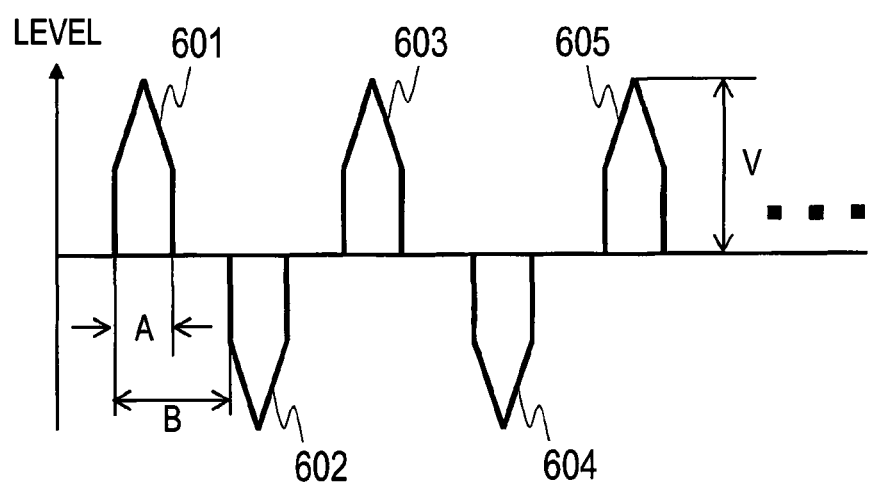
FIGS. 6A and 6B are explanatory charts of waveforms according to a second embodiment of the present invention.
Figure 6B:
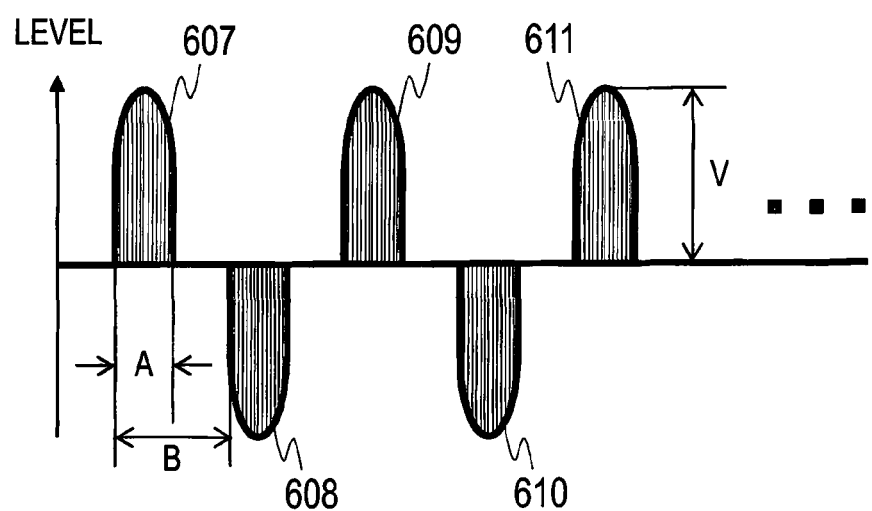

FIG. 6A and FIG. 6B show waveforms according to a second embodiment. In the first embodiment, the level of the synthesized wave pulse continues to rise from the start thereof of the ON state and reaches the maximum at the end time of the ON state where it is then suddenly attenuated. In the second embodiment, each of the synthesized waves shown in FIG. 6A and FIG. 6B are composed of pulses in which the level gradually rises from the point of time when the superimposition of the high frequency is started, reaches the maximum at around an intermediate point of the ON period of the low-frequency pulse and is thereafter attenuated gradually.

FIG. 6A shows such low-frequency synthesized pulse waves 601, 602, 603, 604, 605 . . . (referred to as spear-blade like pulse waves for the sake of convenience), in each of which, during the ON period A, the level gradually rises from the start point, reaches the maximum at around an intermediate point thereof and is then gradually attenuated toward the endpoint of the ON period A. The rise and drop of the level are performed linearly, and each of the low-frequency synthesized pulse waves is formed into a spear tip shape. Thereafter, an interval/pause period, which is a fixed period, is provided, and ON and OFF are repeated in this way over the cycle B, in which positive and negative are alternately repeated in terms of the pulse polarity. In a mode such as the shoulder tapping mode, in which the stimulus is relatively required, the correct effect is observed when this type of the spear-like waveform is used. Moreover, the high-frequency component is superimposed on each ON period of this spear tip-like low frequency waveform, whereby a massage effect not only for the surface muscle but also the deep muscle, and the like can also be expected.

Moreover, FIG. 6B is the same as FIG. 6A in that, with Regard to each of pulse waves 607, 608, 609, 610, 611 . . . (referred to as rounded pulse waves for the sake of convenience), during the ON period A, the level gradually rises from the start point thereof, reaches the maximum at around the intermediate point and is gradually attenuated toward the end point. However, the rise and drop of the level from the point of time when the superimposition of the high-frequency wave is superimposed are not simply linear, and each of the pulse waves is formed into a rounded pulse waveform that is non-linearly expanded. From a synthesized waveform created by superimposing the high-frequency components on the low-frequency waveform as described above, the stimulus feeling is only sensed for a short period of time. Therefore, the cycle B can be extended by constantly maintaining the level V at the maximum point, whereby the resulting waveform is suitable for therapies requiring longer periods of stimulation such as treatment for rehabilitation and the like.

As described above, the waveforms shown in FIG. 6A and FIG. 6B are composed so that the level of each synthesized wave can gradually rise from the point of time when the superimposition is started, reaches the maximum at around the intermediate point of the ON period of the low-frequency pulse, and thereafter, be gradually attenuated. Therefore, in terms of living body stimulation, such a feeling is obtained in which the stimulus rises gradually and is gradually weakened after the maximum point is passed. In such a way, it is made possible to obtain variable soft stimulation effects having less of a prickling feeling (sticking).

Other Embodiments

Note that it is effective even if a waveform generation device and a living body stimulation device, each of which is formed of an arbitrary combination of the above-described constituent elements, are turned to other aspects within the scope of the invention, i.e., other therapy, rehabilitation, massage and beauty, and the like.

What is claimed is:

1. An electrical living body stimulation signal waveform generation device comprising:
   a waveform generation unit configured to generate a low-frequency pulse signal wave of a frequency of less than 1 KHz and a high-frequency signal wave of a frequency of 10 KHz or more individually, the low-frequency pulse signal wave being a pulse wave created by synthesizing a rectangular wave and a gradual increase wave having a non-linearly increased waveform of the same cycle, a level of the low-frequency pulse signal wave being raised instantaneously and thereafter non-linearly increased so that the low-frequency pulse signal wave is a sword-like synthesized pulse wave; and
   a waveform synthesis circuit configured to superimpose the high-frequency signal wave on the low-frequency pulse signal wave during an ON period of the low-frequency pulse signal wave to form a synthesized wave having a waveform in which a level gradually rises from a point of time when the superimposition is started and the ON period and an OFF period of the low-frequency pulse signal wave are continuously repeated,
   wherein the synthesized wave is given as an electrical stimulus to a living body.

2. The electrical living body stimulation signal waveform generation device according to claim 1, wherein the low-frequency pulse signal wave is a pulse wave created by synthesizing a rectangular wave, a tooth-like wave and a sine wave.

3. The electrical living body stimulation signal waveform generation device according to claim 1, wherein the level of the synthesized wave gradually rises from the point of time when the superimposition is started, reaches a maximum at a point of time when the superimposition is ended, and is attenuated after the point of time when the superimposition is ended.

4. The electrical living body stimulation signal waveform generation device according to claim 1, wherein the level of the synthesized wave gradually rises from the point of time when the superimposition is started, reaches a maximum at around an intermediate point of the ON period of the low-frequency pulse signal, and is thereafter gradually attenuated.

5. The electrical living body stimulation signal waveform generation device according to claim 1, further comprising:
   a waveform output control unit configured to change a cycle of the low-frequency pulse signal wave.

6. An electrical living body stimulation device comprising:
   a waveform generation unit configured to generate a low-frequency pulse signal wave of a frequency of less than 1 KHz and a high-frequency signal wave of a frequency of 10 KHz or more individually, the low-frequency pulse signal wave being a pulse wave created by synthesizing a rectangular wave and a gradual increase wave having a non-linearly increased waveform of the same cycle, a level of the low-frequency pulse signal wave being instantaneously raised and thereafter non-linearly increased so that the low-frequency pulse signal wave is a sword-like synthesized pulse wave;
   a waveform synthesis circuit configured to superimpose the high-frequency signal wave on the low-frequency pulse signal wave during an ON period of the low-frequency pulse signal wave to form a synthesized wave in which a level gradually rises from a point of time when the superimposition is started;
   an output control circuit configured to set an output level of the synthesized wave; and a microcomputer configured to control the waveform generation unit, the waveform waveform synthesis circuit and the output control circuit so as to control at least any of a plurality of parameters including the output level of the synthesized wave, a rising rate of the output level, and a cycle and ON/OFF periods of the low-frequency pulse signal wave, wherein the synthesized wave is given as an electrical stimulus to a living body.

7. An electrical living body stimulation signal waveform generation device comprising:

a waveform generation unit configured to generate a low-frequency pulse signal wave of a frequency of less than 1 KHz and a high-frequency signal wave of a frequency of 10 KHz or more individually, the low-frequency pulse signal wave being a pulse wave created by adding a rectangular wave and a gradual increase wave having a non-linearly increased waveform of the same cycle, a level of the low frequency pulse signal starting at zero voltage at a time t0 and increasing instantaneously to a non-zero voltage v1 at a time t1 that occurs after the time t0, and then increasing in a non-linear manner from the time t1 to a time t2 that occurs after the time t1 to cause the level of the low frequency pulse signal to increase non-linearly from the voltage v1 to a voltage v2 greater than the voltage v1 between the time t1 and the time t2, and then the level of the low frequency pulse signal decreasing instantaneously from the voltage v2 to the zero voltage at a time t3 that occurs after the time t2; and a waveform synthesis circuit configured to superimpose the high-frequency signal wave on the low-frequency pulse signal wave during an ON period of the low-frequency pulse signal wave to form a synthesized wave having a waveform in which a level gradually rises from a point of time when the superimposition is started and the ON period and an OFF period of the low-frequency pulse signal wave are continuously repeated, wherein the synthesized wave is given as an electrical stimulus to a living body.

8. The electrical living body stimulation signal waveform generation device according to claim 7, wherein the gradual increase wave is a sinusoidal wave such that the addition of the rectangular wave and the sinusoidal wave creates the low-frequency pulse signal wave having a sword-like shape for each pulse of the low-frequency pulse signal wave.

9. The electrical living body stimulation signal waveform generation device according to claim 7, wherein the non-linearly increase from the voltage v1 to the voltage v2 is a sinusoidal increase.

* * * * *